United States Patent [19]

Jakubowski

[11] Patent Number: 4,612,328

[45] Date of Patent: Sep. 16, 1986

[54] ADMIXTURES OF 2-BROMO-2-BROMOMETHYLGLUTARONITRILE AND METHYLENE BIS(THIOCYANATE)

[75] Inventor: John A. Jakubowski, Piscataway, N.J.

[73] Assignee: Calgon Corporation, Pittsburgh, Pa.

[21] Appl. No.: 679,430

[22] Filed: Dec. 7, 1984

[51] Int. Cl.[4] .................... A01N 47/40; A01N 47/48
[52] U.S. Cl. ........................ 514/515; 71/67;
523/122; 524/206; 524/236
[58] Field of Search .............. 71/67; 514/515

[56] References Cited

U.S. PATENT DOCUMENTS

| | | |
|---|---|---|
| 3,300,375 | 1/1967 | Webner .................. 514/516 |
| 3,524,871 | 8/1970 | Matt ...................... 260/454 |
| 3,644,380 | 2/1972 | Harmetz et al. ......... 260/294.9 |
| 3,833,731 | 9/1974 | Grier et al. ............. 71/67 |
| 3,833,743 | 9/1974 | Morse et al. ........... 426/195 |
| 3,873,597 | 3/1975 | Harmetz et al. ........ 260/465.7 |
| 3,877,922 | 4/1975 | Grier et al. ............. 71/67 |
| 3,929,585 | 12/1975 | Swigert ................. 260/465.7 |
| 3,996,378 | 12/1976 | Payton .................. 514/516 |

*Primary Examiner*—Allen J. Robinson
*Attorney, Agent, or Firm*—William C. Mitchell; R. Brent Olson; Michael C. Sudol, Jr.

[57] ABSTRACT

The instant invention is directed to synergistic antimicrobial admixtures comprising 2-bromo-2-bromomethylglutaronitrile and methylene bis(thiocyanate) and its use in inhibiting microbial growth.

4 Claims, No Drawings

ADMIXTURES OF 2-BROMO-2-BROMOMETHYLGLUTARONITRILE AND METHYLENE BIS(THIOCYANATE)

BACKGROUND OF THE INVENTION

U.S. Pat. Nos. 3,833,731; 3,877,922; 3,873,597; 3,644,380; 3,833,743; and 3,929,858 (which are hereby incorporated by reference) disclose 2-bromo-2-bromomethylglutaronitrile and its use as an antibacterial, antifungal, and algicidal agent.

U.S. Pat. Nos. 3,996,378; 3,300,375; and 3,524,871 (which are hereby incorporated by reference) disclose methylene bis(thiocyanate).

Both 2-bromo-2-bromomethylglutaronitrile and methylene bis(thiocyanate) are known individually as antimicrobial agents. The unexpected finding of the instant invention is that they are synergistic in combination as antimicrobial agents.

DESCRIPTION OF THE INVENTION

The present invention is directed to synergistic antimicrobial admixtures comprising 2-bromo-2-bromomethyleneglutaronitrile hereinafter referred to as "BBMG") and methylene bis(thiocyanate) (hereinafter referred to as "MBT").

The present invention is also directed to a method of inhibiting microbial growth, comprising contacting said growth with an admixture of BBMG and MBT.

As used herein, the phrases "antimicrobial" and "inhibiting microbial growth" describe the killing of, as well as the inhibition of or control of the growth of bacteria, yeasts, fungi, and algae. A number of important industries can experience serious adverse effects from the activity of such bacteria and fungi on the raw materials which they employ, on various aspects of their manufacturing activities, or on the finished products which they produce. Such industries include the paint, wood, textile, cosmetic, leather, tobacco, fur, rope, paper, pulp, plastics, fuel, oil, rubber, and machine industries. Important applications of the synergistic antimicrobial combination of the present invention include: inhibiting the growth of bacteria and fungi in aqueous paints, adhesives, latex emulsions, and joint cements; preserving wood; preserving cutting oils; controlling slime-producing bacteria and fungi in pulp and paper mills and cooling towers; as a spray or dip treatment for textiles and leather to prevent mold growth; as a component of anti-fouling paints to prevent adherence of fouling organisms; protecting paint films, especially exterior paints, from attack by fungi which occurs during weathering of the paint film; protecting processing equipment from slime deposits during manufacture of cane and beet sugar; preventing microorganism buildup and deposits in air washer or scrubber systems and in industrial fresh water supply systems; controlling microorganism contamination and deposits in oil field drilling fluids and muds, and in secondary petroleum recovery processes; preventing bacterial and fungal growth in paper coating processes which might adversely affect the quality of the paper coating; controlling bacterial and fungal growth and deposits during the manufacture of various specialty boards, e.g., cardboard and particle board; preventing sap stain discoloration on freshly cut wood of various kinds; controlling bacterial and fungal growth in clay and pigment slurries of various types which are manufactured for later use in paper coating and paint manufacturing for example, and which are susceptible to degradation by microorganisms during storage and transport; as a hard surface disinfectant to prevent growth of bacteria and fungi on walls, floors, etc.; and in swimming pools to prevent algae growth. The control of bacteria and fungi in pulp and paper mill water systems which contain aqueous dispersions of papermaking fibers is especially important. The uncontrolled buildup of slime produced by the accumulation of bacteria and fungi causes offgrade production, decreased production due to breaks and greater cleanup frequency, increased raw material usage, and increased maintenance costs. The problem of slime deposits has been aggravated by the widespread use of closed white water systems in the paper industry.

Another important area where control of bacterial and fungal growth is vital is in clay and pigment slurries. These slurries are of various clays, e.g. kaolin, and pigments, e.g. calcium carbonate and titanium dioxide, and are manufactured usually at a location separate from the end use application, in for example, paper coating and paint manufacturing, and are then stored and held for later transport to the end use location. Because of the high quality standards for the paper and paint final products in which the slurry is used, it is essential that the clay or pigment slurry have a very low microorganism count or content so that it is usable in the paper coating or paint manufacturing.

The synergistic antimicrobial combination of the present invention may also be utilized for agricultural and animal health applications, for example in preventing or minimizing the growth of harmful bacterial, yeast, and/or fungi on plants, trees, fruit, seeds, or soil. The synergistic combination is especially useful in treating seed to prevent microorganism, particularly fungal attack. The synergistic combination is also useful in protecting animal dip compositions against the buildup of microorganisms, and for this purpose may be combined with a veterinary animal dip parasiticide and an acceptable carrier.

The synergistic combination of the present invention has been found especially useful in controlling the harmful effects of microorganisms in water or aqueous media. Systems which utilize circulating water or aqueous media become infected with microorganisms and experience substantial impairment of their efficiency when deposits of the microorganisms build up in the system. The deposits, called slimes, coat the walls of tanks and other vessels, and any machinery or processing equipment which is employed, and create blockages in pipes and valves. The slimes also create discolorations and other imperfections in any products being produced, forcing costly shutdowns. Control of microorganisms in aqueous media is particularly important where there are dispersed particles or fines in the aqueous media, e.g., dispersed cellulosic fibers and dispersed fillers and pigments in papermaking, and dispersed pigments in paint manufacture.

DETAILED DESCRIPTION OF THE INVENTION

The present invention is directed to a synergistic antimicrobial admixture comprising 2-bromo-2-bromomethylglutaronitrile and methylene bis(thiocyanate).

The present invention is also directed to a method of inhibiting microbial growth, comprising contacting the microbial growth with an admixture of 2-bromo-2- bromomethylglutaronitrile and methylene bis(thiocyanate).

The proportions of the two components of the synergistic combination are dictated by the dosage levels of each component, based on 100% active ingredient, which will be employed in each end use application. The recommended dosage levels are described in detail below.

The synergistic antimicrobial combination active ingredient of the antimicrobial composition of the present invention may be used in diverse formulations: solid, including finely divided powders and granular materials; as well as liquid, such as solutions, emulsions, suspensions, concentrates, emulsifiable concentrates, slurries and the like, depending upon the application intended, and the formulation media desired. Further, when the synergistic antimicrobial combination is liquid, it may be employed neat or may be incorporated into various formulations, both solid and liquid, as an adsorbate on suitable inert carriers such as talc, clays, diatomaceous earth and the like.

Thus, it will be appreciated that the synergistic antimicrobial combination may be employed to form antimicrobial formulations containing the combination as the essential active ingredient, which formulations may also contain a variety of carrier materials adaptable to industrial and agricultural applications including finely divided dry or liquid diluents, extenders, clays, diatomaceous earth, talc and the like, or water and various organic liquids such as loweralkanols, kerosene, benzene, toluene and other petroleum distillate fractions or mixtures thereof.

It will be understood also that the synergistic antimicrobial combination active ingredients may be used in combination with other antimicrobial materials. For example, the combination can be combined with other fungicides and bactericides such as 2-(4'-thiazolyl)benzimidazole, sorbic acid, propionic acid, mycostatin, sodium diacetate, trichomycin, amphotericin, griseofulvin, undecylenic acid, esters of parahydroxybenzoic acid, chlorguinaldol, 5,7-dichloro-8-hydroxyquinoline, sodium-o-phenylphenate, o-phenylphenol, biphenyl chlorinated phenols, sodium benzoate in appropriate concentrations and in appropriate instances so as to combine the action of each to obtain particularly useful results. Such combinations might find particular application in the preparation of germicidal soaps, in the production of cosmetics and aqueous coatings and in combatting paper mill slime accumulations. It is quite clear also that the synergistic antimicrobial combination can be combined with other algicidal agents such as benzalkonium chlorides and other quaternary ammonium compounds to obtain formulations particularly suitable to special problems of algae control.

In accordance with the present invention there is still further provided a method of inhibiting the growth of at least one of: bacteria, yeast, fungi, and algae, comprising contacting said bacteria, yeast, fungi, or algae, with a bactericidally, fungicidally, or algicidally effective amount of the synergistic antimicrobial combination comprising BBMG and MBT.

The antimicrobial methods of treatment of the present invention involve contacting the microorganisms involved with the synergistic antimicrobial combination. This can be accomplished either by simple addition of the two components of the combination together as a single composition, or by addition of the two components separately. Such separate co-administration can either be at the same time or at different times. The net effect will be the same: the article or system being treated will ultimately have incorporated therein or have applied thereto the desired dosage concentration of each component.

As noted above, the instant invention is based upon the discovery that the synergistic antimicrobial combination described above is effective in controlling the growth of bacteria, yeast, fungi and algae in a variety of industrial and agricultural applications. It has been found, for example, that the combination is an effective antimicrobial for the destruction or control of soil fungi and bacteria and for the protection of seeds, bulbs and plants. Also, it is an effective algicide in the treatment of pools and ponds, cooling water systems and the like. The utility of the synergistic antimicrobial combination of this invention is shown not only by its activity against bacteria and fungi responsible for stunting growth, and even destruction of many types of crop-producing plants, but also against those causing degradation and deterioration of many types of industrial products including, for example, paper, leather, wood preservation, textiles, aqueous systems such as adhesives, resins, drilling fluids, pigment dispersions and latex paints and oleoresinous coatings whose films are particularly vulnerable to the destructive action of fungi. The large economic losses encountered in paper-making operations caused by the accumulation of bacterial and fungal slimes in various parts of the system can be eliminated to a significant extent by use of the synergistic combination described herein.

The antimicrobial activity of the compounds described above has been confirmed using standard laboratory techniques. They have been found effective, for example, in inhibiting bacteria. including *Aerobacter aerogenes*, *Pseudomonas* species including *fluorescens* and *aeruginosa*, and *Escherichia coli*. They have been found effective also against fungi including *Penicillium* species, *Saccharomyces* species, *Candida* species, *Fusarium* species, and *Cephalosporium* species. Such bacteria and/or fungi commonly are found on cereal and grain products, in clay and pigment slurries, on oils, on fruits and vegetables and on cosmetics, leather, electrical insulation, textiles and numerous other materials capable of supporting their growth. Also, such bacteria and/or fungi may be found on plants, seeds, fur and wood and in soils. Further, they may be used to control overgrowth of algae such as *Chlorella* sp. including *C. pyrenoidosa*.

As noted above, it has been found that growth of various harmful fungi and bacteria existing in soil is eliminated or limited by use of formulations containing the synergistic antimicrobial combination described herein. The term "soil" as used here is intended to include all media capable of supporting growth of plants and may include humus, sand, manure, compost, artificially created plant growth solutions and the like.

The synergistic antimicrobial combination described above has activity against bacteria, yeast, fungi, and algae when employed at appropriate levels of concentration and may be used to inhibit growth of these organisms. It will be obvious to those skilled in the art that the required effective concentration will vary with particular organisms and in particular applications. In general, however, effective fungicidal, bactericidal and algicidal response is obtained when the synergistic antimicrobial combination is employed in concentrations ranging between 10 and 50,000 ppm (parts per million)

preferably 100 to 15,000 of BBMG and between 5 and 10,000 ppm of MBT, preferably 50 to 10,000, and in a weight ratio of BBMG:MBT of 20:1 to 1:10, preferably 10:1 to 1:5.

Generally, the concentration of MBT required for bactericidal activity will be lower than the concentration required for fungicidal activity. The ranges of concentrations recited above reflect this difference.

For other applications of the type described above, amounts of from 0.005 to 0.30% by weight, based on weight of the substrate being treated, of the synergistic antimicrobial combination of the present invention is incorporated into, sprayed onto, used to dip, or otherwise applied to the substrate to be treated in order to prevent growth of bacteria, fungi, yeasts, and algae.

Following is a table summarizing the dosage ranges for the components of the synergistic antimicrobial combination of the present invention in various types of end uses:

| Application | Concentration (ppm) BBMG[a] | Concentration (ppm) MBT[b] | Preferred Ratio BBMG:MBT |
|---|---|---|---|
| Metalworking Fluids | 100–1,000 pref. 100–500 | 200–650 pref. 100–500 | 10:1–1:1 pref. 5:1–1:2.5 |
| Latex Paints and Emulsions | 100–1,000 pref. 250–500 | 200–650 pref. 50–2,000 | 20:1–1:1 pref. 10:1–2.5:1 |
| Clay & Pigment Slurries | 10–250 | 40–100 | |
| Adhesives | 100–1,000 pref. 250–400 | 200–650 pref. 100–250 | 10:1–1:10 pref. 4:1–1:1 |
| Paper Coatings | 50–250 | 40–100 | |
| Wood Preservation | 1,000–50,000 pref. 1,900–30,000 | 1,900–3,900 pref. 600–10,000 | 10:1–1:1 pref. 3:1 |

[a]BBMG = 2-bromo-2-bromomethylglutaronitrile
[b]MBT = methylene bis(thiocyanate)

Of course, the precise dosages of the components which will be employed depends upon a number of factors. First, the dosage is indicated in parts per million (ppm), which refers to the concentration of the active ingredient in the environment being treated, for example, the concentration of BBMG in a clay slurry. This concentration is based on 100% active ingredient for convenience in evaluating and comparing test data. In actual practice, however, various percentages of active ingredient may actually be used, with the balance of the composition being added comprising conventional excipients such as dispersants, stabilizers, preservatives, co-solvents, diluents, and the like.

The components of the synergistic antimicrobial combination of the present invention may be added to an article or system to be treated as separate entities, or as a combination. The two components are physically and chemically compatible and may be combined simply as active ingredients, or may additionally be combined with commonly employed carriers and excipients, as described above.

The following example, which was actually carried out, will serve to further illustrate the present invention, without at the same time, however, constituting any limitation thereof.

EXAMPLES

Aqueous Paint and Adhesive

Biocides were added separately and individually to 50 gram aliquots of the aqueous paint and adhesive as shown in Tables 1 and 2. Each aliquot was inoculated with a mixed suspension (approximately $5 \times 10^6$ microorganisms/gram of substrate). The samples were incubated at 28°–30° C. and were streaked on Sabouraud Maltose agar petri lates at intervals of 24, 48, 72 hours and seven days after inoculation. All plates were incubated at 28°–30° C. for seven days. The results are reported in Tables I and II.

The microorganisms used in the tests were:
Pseudomonas stutzeri
Pseudomonas fluorescens; bacteria
Pseudomonas aeruginosa
Saccharomyces cerevisiae; yeast
Aspergillus niger; fungi
Penicillium funiculosum

Metalworking Fluids

Petroleum base soluble and synthetic metalworking fluids were diluted 1 part oil: 40 parts tap water. Biocides were added separately and individually to 300 ml aliquots of each test system. inoculations of bacteria, yeasts and fungi were made weekly (approximately $5 \times 10^6$ microorganisms/gram of substrate) and the microbial population was analyzed once/week for 105 days (15 weeks) using conventional plate count techniques. Table 3 shows the number of days of inhibition provided by the biocides individually and in combination. Plate counts of $10^5$ for two consecutive weeks were considered as failures.

The microorganisms used in the tests were:
Pseudomonas aeruginosa
Pseudomonas fluorescens
Saccharomyces cerevisiae
Candida sp.
Fusarium sp.
Cephalosporium sp.

Sap Stain Wood Preservatives

Solutions of 0.25, 0.5, 1.0, 2.0, 4.0% biocides were prepared in appropriate solvent/water mixtures to provide desired concentrations. Six replicates of test specimens of both soft and hardwood ($\frac{1}{4}'' \times 3/5'' \times 2\frac{3}{4}''$ in size) were treated by a 20 seconds dip into the biocide solutions. The untreated controls were dipped into a solvent/water blank. Harwood, (birch sapwood) and softwood, (northern pine sapwood) were used in the tests to cover both types of lumber substrates. After 24 hours air drying, the six specimens from each treatment group were subjected to a weathering procedure. The procedure consisted of two hours leaching in running water followed by four hours of heat exposure at 105° F. After 24 hours air drying, the wood samples were placed into petri dish chambers. Each dish contained a filter paper disc, 15 ml water and a curved 3 mm glass rod. Two treated test specimens were placed on top of the glass rod in each petri dish. The test samples were inoculated with a spore suspension of the following stain fungi:
Trichoderma viride
Cladosporium herbarum
Aspergillus fumigatus
Pullularia pullulans

*Ceratocystis pilifera*
*Cephaloascus fragrans*

The test was incubated at 26°–28° C. and 85% relative humidity for 28 days. At the end of the incubation period, all samples were visually observed for the extent of fungal growth. The test results are presented in Table 4.

TABLE 1

Preservation Properties of Combinations of 2-Bromo-2-Bromomethylglutaronitrile and Methylene bis(thiocyanate) in Latex Paint

| Example | ppm | Biocide | 24 hr | 48 hr | 72 hr | 7 days |
|---|---|---|---|---|---|---|
| 1 | 250 | BBMG[a] | 4 | 4 | 4 | 4 |
| 2 | 500 | BBMG | 4 | 4 | 4 | 4 |
| 3 | 750 | BBMG | 4 | 4 | 4 | 4 |
| 4 | 1,000 | BBMG | 2 | 1 | 0 | 0 |
| 5 | 1,500 | BBMG | 0 | 0 | 0 | 0 |
| 6 | 250 | MBT[b] | 4 | 4 | 4 | 4 |
| 7 | 500 | MBT | 4 | 4 | 4 | 4 |
| 8 | 1,000 | MBT | 4 | 4 | 4 | 4 |
| 9 | 2,000 | MBT | 4 | 4 | 3 | 1 |
| 10 | 250 / 100 | BBMG + MBT | 3 | 1 | 0 | 0 |
| 11 | 100 / 100 | BBMG + MBT | 4 | 4 | 4 | 4 |
| 12 | 100 / 500 | BBMG + MBT | 4 | 4 | 4 | 4 |
| 13 | 500 / 50 | BBMG + MBT | 1 | 0 | 0 | 0 |
| 14 | | Latex Paint - no biocide | 4 | 4 | 4 | 4 |

[a]BBMG = 2-bromo-2-bromomethylglutaronitrile
[b]MBT = methylene bis(thiocyanate)
Legend
4 = Heavy microbial growth
3 = Moderate microbial growth
2 = Light microbial growth
1 = Trace microbial growth
0 = Sterile; no growth

TABLE 2

Preservation Properties of Combinations of 2-Bromo-2-Bromomethylglutaronitrile and Methylene bis(thiocyanate) in Adhesive

| Example | ppm | Biocide | 24 hr | 48 hr | 72 hr | 7 days |
|---|---|---|---|---|---|---|
| 15 | 100 | BBMG[a] | 4 | 4 | 4 | 4 |
| 16 | 250 | BBMG | 4 | 4 | 4 | 4 |
| 17 | 500 | BBMG | 4 | 4 | 4 | 4 |
| 18 | 750 | BBMG | 2 | 2 | 0 | 0 |
| 19 | 1,000 | BBMG | 1 | 0 | 0 | 0 |
| 20 | 100 | MBT[b] | 4 | 4 | 4 | 4 |
| 21 | 250 | MBT | 4 | 4 | 4 | 4 |
| 22 | 500 | MBT | 4 | 4 | 4 | 4 |
| 23 | 750 | MBT | 3 | 3 | 2 | 2 |
| 24 | 1,000 | MBT | 2 | 0 | 0 | 0 |
| 25 | 400 / 100 | BBMG + MBT | 0 | 0 | 0 | 0 |
| 26 | 250 / 250 | BBMG + MBT | 0 | 0 | 0 | 0 |
| 27 | 250 / 100 | BBMG + MBT | 4 | 3 | 1 | 0 |
| 28 | 100 / 100 | BBMG + MBT | 4 | 4 | 4 | 4 |
| 29 | | Adhesive - no biocide | 4 | 4 | 4 | 4 |

[a]BBMG = 2-bromo-2-bromomethylglutaronitrile
[b]MBT = methylene bis(thiocyanate)
Legend
4 = Heavy microbial growth
3 = Moderate microbial growth
2 = Light microbial growth
1 = Trace microbial growth
0 = Sterile; no growth

TABLE 3

Preservation Properties of 2-Bromo-2-Bromomethylglutaronitrile and Methylene bis(thiocyanate) in Metalworking Fluids

| | | | Days of Inhibition | |
|---|---|---|---|---|
| Example | ppm | Biocide | Soluble Fluid | Synthetic Fluid |
| 30 | 100 | BBMG | 0 | 0 |
| 31 | 250 | BBMG | 14 | 7 |
| 32 | 500 | BBMG | 56 | 49 |
| 33 | 750 | BBMG | 84 | 63 |
| 34 | 1,000 | BBMG | 105 | 105 |
| 35 | 100 | MBT | 0 | 0 |
| 36 | 250 | MBT | 0 | 0 |
| 37 | 500 | MBT | 56 | 14 |
| 38 | 750 | MBT | 56 | 14 |
| 39 | 1,000 | MBT | 84 | 28 |
| 40 | 100 / 100 | BBMG + MBT | 35 | 28 |
| 41 | 250 / 250 | BBMG + MBT | 49 | 56 |
| 42 | 250 / 250 | BBMG + MBT | 105 | 105 |
| 43 | 500 / 100 | BBMG + MBT | 105 | 105 |
| 44 | 250 / 500 | BBMG + MBT | 105 | 105 |
| 45 | 100 / 250 | BBMG + MBT | 35 | 28 |

TABLE 4

Sapstain and Mold Control of Pine and Birch Sapwood Treated with Various Fungicide Solutions

| | | | Sapstain and Mold Control Results | |
|---|---|---|---|---|
| Example | ppm | Biocide | Pine Sapwood | Birch Sapwood |
| 46 | 2,500 | MBT | 4 | 4 |
| 47 | 5,000 | MBT | 2 | 1 |
| 48 | 10,000 | MBT | 0 | 0 |
| 49 | 20,000 | MBT | 0 | 0 |
| 50 | 40,000 | MBT | 0 | 0 |
| 51 | 2,500 | BBMG | 4 | 4 |
| 52 | 5,000 | BBMG | 4 | 4 |
| 53 | 10,000 | BBMG | 4 | 4 |
| 54 | 20,000 | BBMG | 4 | 2 |
| 55 | 40,000 | BBMG | 0 | 0 |
| 56 | 1,900 / 600 | BBMG/MBT | 3 | 1 |
| 57 | 3,700 / 1,300 | BBMG/MBT | 0 | 0 |
| 58 | 7,500 / 2,500 | BBMG/MBT | 0 | 0 |
| 59 | 15,000 / 5,000 | BBMG/MBT | 0 | 0 |
| 60 | 30,000 / 10,000 | BBMG/MBT | 0 | 0 |
| 61 | | Control - No treatments | 4 | 4 |

Legend
4 = Heavy microbial growth
3 = Moderate microbial growth
2 = Light microbial growth
1 = Trace microbial growth
0 = Sterile; no growth

What is claimed is:

1. A method of inhibiting microbial growth, wherein said microbial growth is selected from the group consisting of *Pseudomonas stutzen, Pseudomonas Fluorescens, Pseudomonas aeruginosa, Saccharomyces cerevisiae, Aspergillus niger, Penicillivm funiculosum, Candida sp., Fusarium sp., Cephelosporium sp., Trichoderma viride, Cladosporium herbarum, Aspergillus fumigatus, Pullularia pullulans, Ceratocystic pilifera, Cephaloascus fragrans* and mixtures thereof, comprising contacting said microbial growth with an effective amount of an admixture comprising:

(a) 2-bromo-2-bromomethylglutaronitrile and
(b) methylene bis(thiocyanate),
wherein the weight ratio of (a):(b) ranges from about 1:2.5 to 10:1.

2. The method of claim 1, wherein said admixture further comprises a carrier.

3. A synergistic antimicrobial admixture comprising:
(a) 2-bromo-2-bromomethylglutaronitrile and
(b) methylene bis(thiocyanate),
wherein the weight ratio of (a):(b) ranges from about 1:2.5 to 10:1.

4. The admixture of claim 3, further comprising a carrier.

* * * * *